United States Patent [19]

Futcher

[11] Patent Number: 4,995,900

[45] Date of Patent: Feb. 26, 1991

[54] HERBICIDAL AQUEOUS BASED MICROEMULSION COMPOSITIONS

[75] Inventor: Ian Futcher, Fareham, United Kingdom

[73] Assignee: American Cyanamid Company, Stamford, Conn.

[21] Appl. No.: 278,302

[22] Filed: Nov. 30, 1988

[51] Int. Cl.$^5$ ............................................. A01N 43/48
[52] U.S. Cl. ..................................... 71/92; 71/DIG. 1
[58] Field of Search ............................... 71/92, DIG. 1

[56] References Cited

U.S. PATENT DOCUMENTS

| | | | |
|---|---|---|---|
| 3,867,403 | 2/1975 | Feeny | 260/311 |
| 3,922,161 | 11/1975 | Walworth et al. | 71/92 |
| 4,170,464 | 10/1979 | Feeny | 71/92 |
| 4,529,436 | 7/1985 | Pasarela | 71/92 |

FOREIGN PATENT DOCUMENTS 1164321  9/1969  United Kingdom ........... 71/DIG. 1

OTHER PUBLICATIONS

The Royal Society of Chemistry, *The Agrochemicals Handbook*, (ed. Hartley et al.), 1983.

*Primary Examiner*—Richard L. Raymond
*Assistant Examiner*—Brian Mo Burn
*Attorney, Agent, or Firm*—John W. Hogan, Jr.

[57] ABSTRACT

Herbicidal aqueous microemulsions of difenzoquat methyl sulfate, an essentially water insoluble active ingredient, and a nonionic surfactant demonstrate increased stability.

7 Claims, No Drawings

HERBICIDAL AQUEOUS BASED MICROEMULSION COMPOSITIONS

BACKGROUND OF THE INVENTION

The present invention relates to novel herbicidal aqueous based microemulsions and methods for preparing the microemulsions.

Aqueous pesticidal formulations have attracted considerable interest in recent years because they possess certain advantages over non-aqueous formulations. One advantage aqueous formulations (e.g. suspension concentrates, concentrated emulsions and flowables) possess includes the reduction or elimination of organic solvents. This reduction or elimination of organic solvents results in reduced phytotoxicity (encouraged by some organic solvents); decreased costs when compared to organic-based formulations; safer handling; better compatibility with a greater variety of packaging materials; and, in some instances, enhanced biological activity.

Concentrated aqueous emulsions are an alternative to emulsifiable concentrates. Concentrated emulsions are advantageous because of their increased stability over emulsifiable concentrates and ease of use. However, it is known that the high surface area created in preparations of this sort is usually accompanied by large surface free energies. This, in turn, creates the opportunity for a variety of breakdown processes, and therefore, while the kinetic stability of these emulsions (dispersions) may be increased, they still represent thermodynamically-unstable systems.

Microemulsions present a unique class of thermodynamically-stable liquid dispersions. The thermodynamic stability of microemulsions is attributed to the presence of near zero interfacial tensions at equilibrium and also a minimum or potentially negative Gibbs free-energy term for the system. In order to achieve low interfacial tensions, the use of several surfactants is usually required. When one of the surfactants is soluble in the water phase and the other is soluble in the organic phase, each one has only a marginal effect on the other, and their combined effect may be large enough to reduce the interfacial tension to near zero at finite concentrations. As a rule microemulsions are difficult to formulate and are obtainable only with certain surfactant combinations and only within specific finite concentrations of these surfactant combinations. However, because microemulsions offer the greatest potential stability for formulations of this kind, there is an ongoing search in the art for microemulsion compositions.

SUMMARY OF THE INVENTION

The present invention relates to certain novel aqueous herbicidal microemulsion compositions containing 1,2-dimethyl-3,5-diphenylpyrazolium also called difenzoquat and methods for preparing the compositions.

Surprisingly, it has been found that the aqueous microemulsions of difenzoquat and at least one essentially water insoluble herbicide or fungicide require only one surfactant. The microemulsion compositions of this invention demonstrate increased physical stability. These microemulsions also remain chemically stable for extended periods of time and are particularly useful for controlling a broad range of undesirable plant species, such as wildoats and broad leaf weeds and fungi.

The microemulsions of the present invention are comprised on a weight to volume basis of about 20% to 40% of a 1,2-dimethyl-3,5-diphenylpyrazolium salt; about 5% to 25% of at least one essentially non-aqueous soluble herbicidally or fungicidally active ingredient; about 5% to 40% of a nonionic surfactant; and 0% to 25% of adjuvants such as antifoaming agents, anti-freezing agents, crystal modifying agents, viscosity adjusting agents (thickening agents), buffer and pH control agents and antimicrobial preservatives.

DETAILED DESCRIPTION OF THE INVENTION

The 1,2-dimethyl-3,5-diphenylpyrazolium methyl sulfate utilized in the present invention is a known herbicide. Although other salts may be employed, the methyl sulfate salt is preferred.

A variety of other essentially water insoluble active ingredients may be used in accordance with the present invention. Advantageously, herbicidally and fungicidally active ingredients which are generally not water soluble are combined with the difenzoquat salt to form the active ingredients of the microemulsion formulation. Herbicidally and fungicidally active ingredients such as esters of 4-chloro-2-methylphenoxyacetic (MCPA) acid bromoxynil esters and esters of 2,4-dichlorophenoxy acetic acid (2,4-D), as well as acetochlor, bupirimate, butylate, chlorbufam, flurochloridone, esters of 2,4-DB acid, any dichlorprop ester, any fenoprop ester, fenpropimorph, fluoroglycofen-ethyl, fluroxypyr, ioxynil esters, esters of MCPB, mecoprop esters, metolachlor, molinate, propiconazole, pyridate, sethoxydim, 2,4,5-T esters, tebutam, triclopyr, and vernolate are useful in the compositions of this invention.

Preferred essentially water insoluble active ingredients include: straight or branched $C_4$–$C_{10}$ alkyl esters of 2,4-D acid and mixtures thereof; straight or branched $C_4$–$C_{10}$ alkyl esters of MCPA acid and mixtures thereof; and/or bromoxynil esters of straight or branched $C_4$–$C_{10}$ alkanoic acids and mixtures thereof. The isoctyl ester of 2,4-D acid, $C_4H_9$ esters (mixed butyl esters) of MCPA acid and bromoxynil octanoate or mixtures thereof are especially preferred.

Aqueous formulations of these herbicidally active ingredients are normally prepared using the salts of these compounds which are water soluble not the esters. However, it has been found in some instance s that an ester can be more effective because many of these essentially water insoluble herbicidally active ingredients are normally applied post-emergence to the foliage of the undesirable plant and the leaf penetration properties of the pesticide can be altered using various lipophilic esters and/or acids of these herbicides. Hence the novel compositions of this invention which comprise a water soluble herbicidal difenzoquat salt with essentially water insoluble herbicides in an aqueous medium provide an additional advantage over other formulations.

Only one surfactant is required in the preparation of the microemulsions of the present invention, although more than one surfactant can be used. A nonionic type of surfactant or wetting agent is preferable. Preferred nonionic surfactants include polyethoxylated alkylphenols with about 6 to 15 moles of ethylene oxide. Octyl phenols such as an ethoxylated octyl phenol with 9.5 moles of ethylene oxide, which is available under the trade name Triton X-100 ®, and nonyl phenols are especially preferred.

A variety of commonly employed agricultural adjuvants known in the art may optionally be employed: for example antifoaming agents; antifreezing agents and crystal modifiers such as urea, glycols and alcohols; viscosity adjusting agents (thickening agents); pH adjustment agents (by ionic buffering and/or acids or alkalis); antimicrobial agents and the like.

The actual quantity of active ingredient technical needed is dependent on the ester or mix of esters, acid or mix of acids, or (in the case of difenzoquat) the anion employed. For instance, preferred compositions can be prepared by admixing the non-herbicidally=active ingredients with: (1) difenzoquat 15%-20% on a cation basis with 8%-12% ester of a phenoxyacetic acid on a free acid (acid equivalent) basis or (2) 15%-20% difenzoquat on a cation basis and 4%-8% bromoxynil esters on a phenol equivalent (free phenol) basis and 4%-8% ester of a phenoxyacetic acid on free acid basis.

Unexpectedly, the microemulsion compositions of the present invention may be readily prepared by admixing the desired amount of herbicidally active and non-active ingredients in any order. The formation of a microemulsion by such a process is unusual because the prior art generally teaches that order of addition of ingredients is important for the formation of a microemulsion and incorrect sequence leads to an unsatisfactory formulation, i.e., no microemulsion is formed.

A preferred method of preparing compositions of the present invention is to first add the difenzoquat salt to an amount of water sufficient to dissolve the difenzoquat and subsequently adding the required quantities of surfactant, adjuvants and other herbicidally active ingredient(s).

The invention is further illustrated in the following non-limiting examples.

EXAMPLES 1-3

Preparation of herbicidal microemulsion compositions containing 1,2-dimethyl-3,5-diphenylpyrazolium salt 1,2-dimethyl-3,5-diphenylpyrazolium methyl sulfate, at about 24.5 kg is added to 15.4 liters of water and agitated until dissolved. To the stirred solution is added, 30 kg of an ethoxylated octyl phenol with 9.5 moles of ethylene oxide, 18 kg of isobutyl alcohol, and 2.0 kg of urea. A specified quantity of essentially water insoluble herbicidally active ingredient(s) listed in TABLE 1 is added to each of three mixtures. The pH of each of the mixtures is adjusted to a range from pH 6 to pH 7 and the resulting mixtures are stirred to yield the desired microemulsions.

TABLE 1

| Example | Quantity | Essentially water insoluble herbicide |
|---|---|---|
| 1 | 15.1 kg | isooctyl ester of 2,4-D acid |
| 2 | 12.8 kg | mixed butyl esters of MCPA |
| 3 | 7.17 kg | mixed butyl esters of MCPA plus |
|   | 8.15 kg | bromoxynil octanoate |

EXAMPLE 4

The physical characteristics of the compositions in Examples 1-3 were evaluated as follows:
1. Determination of translational diffusion coefficient/size (radius) of any droplets present by photon correlation spectroscopy;
2. Determination of the electrical conductivity of the samples;
3. Measurement of the UV/visible spectra of the samples;
4. Determination of state of the dispersion, i.e. water-continuous (o/w dispersion) or oil continuous (w/o dispersion).

The results of these experiments are summarized in TABLE 2 below.

TABLE 2

| Example | Maximum Radius | Conductivity $(K)/S\ cm^{-1}$ | Light Absorption (25° C.) | |
|---|---|---|---|---|
|   |   |   | $A_{488}$ | $A_{344}$ |
| 1 | 90 Å | $1.18 \times 10^{-3}$ | 0.0075 | 3.05 |
| 2 | 90 | $1.49 \times 10^{-3}$ | 0.62 | 3.96 |
| 3 | 150 Å | $1.29 \times 10^{-3}$ | 0.65 | 3.03 |

It has been determined the results of these experiments are consistent with oil-in-water (o/w) microemulsions. No droplets of larger size were detected and there was no observable time dependence of droplet size which suggests that the system is stable. Indeed enhanced stability is one of the hallmarks of the aqueous based microemulsion compositions of the present invention.

EXAMPLES 5-77

Following essentially the same procedure as in Examples 1-3, ingredients are admixed in the percentages listed in TABLE 3 to yield stable microemulsions. In TABLE 3, MCPA MBE means mixed butyl esters of MCPA; MCPA IOE means isoctyl ester of MCPA; 2,4-D IOE means isoctyl ester of 2,4-D; and octyl phenol (9.5 MEO) means an ethoxylated octyl phenol with 9.5 moles of ethylene oxide.

TABLE 3

| Example | Difenzoquat Methyl Sulfate | MCPA MBE | MCPA IOE | Bromoxynil Octanoate | 2,4-D IOE | Octyl Phenol (9.5 MEO) | Isobutyl Alcohol | Urea | Water (to make) |
|---|---|---|---|---|---|---|---|---|---|
| 5 | 24.56 | 7.44 | — | 8.85 | — | 27.5 | 15.0 | 2.5 | 100.0% |
| 6 | 24.56 | 7.44 | — | 8.85 | — | 30.0 | 12.5 | 2.5 | 100.0% |
| 7 | 24.56 | 7.44 | — | 8.85 | — | 30.0 | 15.0 | 2.5 | 100.0% |
| 8 | 24.56 | 7.44 | — | 8.85 | — | 30.0 | 17.5 | 2.5 | 100.0% |
| 9 | 24.56 | 7.44 | — | 8.85 | — | 30.0 | 18.0 | 2.5 | 100.0% |
| 10 | 24.56 | 7.44 | — | 8.85 | — | 32.5 | 10.0 | 2.5 | 100.0% |
| 11 | 24.56 | 7.44 | — | 8.85 | — | 35.0 | 7.5 | 2.5 | 100.0% |
| 12 | 24.56 | 7.44 | — | 8.85 | — | 25.0 | 20.0 | 5.0 | 100.0% |
| 13 | 24.56 | 7.44 | — | 8.85 | — | 27.5 | 12.5 | 5.0 | 100.0% |
| 14 | 24.56 | 7.44 | — | 8.85 | — | 30.0 | 10.0 | 5.0 | 100.0% |
| 15 | 24.56 | 7.44 | — | 8.85 | — | 30.0 | 12.5 | 5.0 | 100.0% |
| 16 | 24.56 | 7.44 | — | 8.85 | — | 30.0 | 15.0 | 5.0 | 100.0% |
| 17 | 24.56 | 7.44 | — | 8.85 | — | 25.00 | 20.00 | — | 100.0% |
| 18 | 24.56 | 7.44 | — | 8.85 | — | 27.50 | 17.50 | — | 100.0% |
| 19 | 24.56 | 7.44 | — | 8.85 | — | 30.0 | 12.5 | — | 100.0% |

TABLE 3-continued

| Example | Difenzoquat Methyl Sulfate | MCPA MBE | MCPA IOE | Bromoxynil Octanoate | 2,4-D IOE | Octyl Phenol (9.5 MEO) | Isobutyl Alcohol | Urea | Water (to make) |
|---|---|---|---|---|---|---|---|---|---|
| 20 | 24.56 | 7.44 | — | 8.85 | — | 30.0 | 15.0 | — | 100.0% |
| 21 | 24.56 | 7.44 | — | 8.85 | — | 30.0 | 17.5 | — | 100.0% |
| 22 | 24.56 | 7.43 | — | 8.85 | — | 30.0 | 17.5 | — | 100.0% |
| 23 | 24.56 | 7.44 | — | 8.85 | — | 30.0 | 20.0 | — | 100.0% |
| 24 | 24.56 | 7.44 | — | 8.85 | — | 32.5 | 12.5 | — | 100.0% |
| 25 | 24.56 | 7.44 | — | 8.85 | — | 35.0 | 10.0 | — | 100.0% |
| 26 | 24.56 | 7.44 | — | 8.85 | — | 37.5 | 7.5 | — | 100.0% |
| 27 | 25.01 | 7.26 | — | 9.06 | — | 30.0 | 18.0 | 2.0 | 100.0% |
| 28 | 25.08 | 7.55 | — | 9.96 | — | 30.0 | 18.0 | 2.0 | 100.0% |
| 29 | 24.57 | 7.33 | — | 9.02 | — | 30.0 | 18.0 | 2.0 | 100.0% |
| 30 | 24.56 | 7.44 | — | 8.85 | — | 30.0 | 15.0 | 5.0 | 100.0% |
| 31 | 24.56 | 7.44 | — | 8.85 | — | 30.0 | 20.0 | 5.0 | 100.0% |
| 32 | 24.56 | — | 8.63 | 8.23 | — | 30.0 | 15.0 | 1.5 | 100.0% |
| 33 | 24.56 | — | 8.63 | 8.23 | — | 30.0 | 17.5 | 1.5 | 100.0% |
| 34 | 24.56 | — | 8.63 | 8.23 | — | 30.0 | 20.0 | 1.5 | 100.0% |
| 35 | 24.56 | — | 8.63 | 8.23 | — | 30.0 | 17.0 | 2.5 | 100.0% |
| 36 | 24.56 | — | 8.63 | 8.23 | — | 30.0 | 15.0 | 3.5 | 100.0% |
| 37 | 24.56 | — | 8.63 | 8.23 | — | 30.0 | 17.5 | 3.5 | 100.0% |
| 38 | 24.56 | — | 8.63 | 8.23 | — | 30.0 | 20.0 | 3.5 | 100.0% |
| 39 | 24.56 | — | 8.63 | 8.23 | — | 30.0 | 15.0 | 4.5 | 100.0% |
| 40 | 24.56 | — | 8.63 | 8.23 | — | 30.0 | 17.5 | 4.5 | 100.0% |
| 41 | 24.56 | — | 8.63 | 8.23 | — | 30.0 | 20.0 | 4.5 | 100.0% |
| 42 | 24.56 | — | 16.59 | — | — | 30.0 | 17.0 | 2.5 | 100.0% |
| 43 | 24.56 | 13.29 | — | — | — | 25.0 | 20.0 | — | 100.0% |
| 44 | 24.56 | 13.29 | — | — | — | 27.5 | 17.5 | — | 100.0% |
| 45 | 24.56 | 13.29 | — | — | — | 30.0 | 15.0 | — | 100.0% |
| 46 | 24.56 | 13.29 | — | — | — | 25.0 | 17.5 | 2.5 | 100.0% |
| 47 | 24.56 | 13.29 | — | — | — | 27.5 | 15.0 | 2.5 | 100.0% |
| 48 | 24.56 | 13.29 | — | — | — | 30.0 | 12.5 | 2.5 | 100.0% |
| 49 | 24.56 | 13.29 | — | — | — | 25.0 | 15.0 | 5.0 | 100.0% |
| 50 | 24.56 | 13.29 | — | — | — | 27.5 | 12.5 | 5.0 | 100.0% |
| 51 | 24.56 | 13.29 | — | — | — | 30.0 | 10.0 | 5.0 | 100.0% |
| 52 | 24.56 | 13.29 | — | — | — | 30.0 | 10.0 | 5.0 | 100.0% |
| 53 | 24.56 | 13.29 | — | — | — | 30.0 | 20.0 | 5.0 | 100.0% |
| 54 | 24.56 | 7.44 | — | 8.85 | — | 30.0 | 10.0 | — | 100.0% |
| 55 | 24.56 | 7.44 | — | 8.85 | — | 25.0 | 17.5 | 2.5 | 100.0% |
| 56 | 24.56 | 7.44 | — | 8.85 | — | 30.0 | 10.0 | 2.5 | 100.0% |
| 57 | 24.56 | 7.44 | — | 8.85 | — | 20.0 | 20.0 | 5.0 | 100.0% |
| 58 | 24.56 | 7.44 | — | 8.85 | — | 25.0 | 15.0 | 5.0 | 100.0% |
| 59 | 24.56 | 7.44 | — | 8.85 | — | 25.0 | 15.0 | 5.0 | 100.0% |
| 60 | 24.56 | 7.44 | — | 8.85 | — | 30.0 | 7.5 | 5.0 | 100.0% |
| 61 | 24.56 | 7.44 | — | 8.85 | — | 30.0 | 10.0 | 5.0 | 100.0% |
| 62 | 24.56 | 7.44 | — | 8.85 | — | 30.0 | 10.0 | 5.0 | 100.0% |
| 63 | 24.56 | 7.44 | — | 8.85 | — | 32.5 | 7.5 | 5.0 | 100.0% |
| 64 | 24.56 | — | — | — | 15.44 | 27.5 | 12.5 | 5.0 | 100.0% |
| 65 | 24.57 | 13.09 | — | — | — | 30.0 | 18.0 | 2.0 | 100.0% |
| 66 | 24.56 | 13.29 | — | — | — | 25.0 | 12.5 | 7.5 | 100.0% |
| 67 | 24.56 | — | — | — | 15.44 | 25.0 | 20.0 | — | 100.0% |
| 68 | 24.56 | — | — | — | 15.44 | 27.5 | 17.5 | — | 100.0% |
| 69 | 24.56 | — | — | — | 15.44 | 30.0 | 15.0 | — | 100.0% |
| 70 | 24.57 | — | — | — | 15.42 | 30.0 | 18.0 | 2.0 | 100.0% |
| 71 | 24.56 | — | — | — | 15.44 | 25.0 | 17.5 | 2.5 | 100.0% |
| 72 | 24.56 | — | — | — | 15.44 | 27.5 | 15.0 | 2.5 | 100.0% |
| 73 | 24.56 | — | — | — | 15.44 | 30.0 | 12.5 | 2.5 | 100.0% |
| 74 | 24.56 | — | — | — | 15.44 | 25.0 | 15.0 | 5.0 | 100.0% |
| 75 | 24.56 | — | — | — | 15.44 | 30.0 | 10.0 | 5.0 | 100.0% |
| 76 | 24.56 | — | — | — | 15.44 | 30.0 | 10.0 | 5.0 | 100.0% |
| 77 | 24.56 | — | — | — | 15.44 | 30.0 | 20.0 | 5.0 | 100.0% |

EXAMPLES 78-80

Following essentially the same procedure as in Examples 1-3, ingredients are admixed in the percentages listed in TABLE 4 to yield stable microemulsions. In Table 4, 2,4-D IOE means isocyl ester of 2,4-D; Nonyl Phenol (6.5 MEO) means an ethoxylated nonyl phenol with 6.5 moles of ethylene oxide; and Nonyl phenol (8 MEO) means an ethoxylated nonyl phenol with 8 moles of ethylene oxide.

TABLE 4

| Example | Difenzoquat Methyl Sulfate | 2,4-D IOE | Nonyl Phenol (6.5 MEO) | Nonyl Phenol (8 MEO) | Nonyl Phenol (8 MEO)* | Urea | NaH$_2$PO$_4$ | Water (to make) |
|---|---|---|---|---|---|---|---|---|
| 78 | 35.1 | 21.5 | 15.0 | 15.0 | — | 5.0 | 1.0 | 100.0 |
| 79 | 25.6 | 16.8 | — | — | 35.0 | 5.0 | 1.0 | 100.0 |
| 80 | 30.7 | 18.9 | — | 35.0 | — | 5.0 | 1.0 | 100.0 |

*90% phenol in 10% isobutyl alcohol

It is understood that many changes can be made to the present invention by one of ordinary skill in the art without departing from the spirit and scope of the present invention as defined in the following claims.

What is claimed is:

1. A herbicidal aqueous-based microemulsion comprising on a weight to volume basis about 20% to 40% of a 1,2-dimethyl-3,5-diphenylpyrazolium salt; about 5% to 25% of at least one essentially water insoluble herbicidally active ingredient selected from the group consisting of esters of 2,4-D acid; about 5% to 40% of at least one nonionic surfactant; and 0% to about 25% of adjuvants.

2. The microemulsion according to claim 1, wherein one surfactant is used.

3. The microemulsion according to claim 2, wherein the 1,2-dimethyl-3,5-diphenylpyrazolium salt is 1,2-dimethyl-3,5-diphenylpyrazolium methyl sulfate.

4. The microemulsion according to claim 1, wherein the 1,2-dimethyl-3,5-diphenylpyrazolium salt is 1,2-dimethyl-3,5-diphenylpyrazolium methyl sulfate.

5. The microemulsion according to claim 4, wherein the surfactant is selected from the group consisting of polyethoxylated alkylphenols with about 6 to 15 moles of ethylene oxide and mixtures thereof.

6. The microemulsion according to claim 5, wherein the surfactant is polyethoxylated octyl or nonyl phenols with 8-10 moles of ethylene oxide or mixtures thereof and the water insoluble active ingredient is selected from the group consisting of straight or branched $C_4$-$C_{10}$ alkyl esters of 2,4-D and mixtures thereof.

7. The microemulsion according to claim 6, comprising on a weight to volume basis about 24% to 25% 1,2-dimethyl-3,5-diphenylpyrazolium methyl sulfate; about 14% to 16% isoctyl ester 2,4-D, about 30% polyethyoxylated octyl phenyl with 9-10 moles of ethylene oxide, about 18% isobutyl alcohol about 2% urea and about 0.01% antifoaming agents.

* * * * *